United States Patent
Eastlack et al.

(10) Patent No.: US 11,497,624 B2
(45) Date of Patent: Nov. 15, 2022

(54) METHODS AND APPARATUS FOR AN INSERTION GUIDE DEVICE

(71) Applicant: Spine Innovation, LLC, Del Mar, CA (US)

(72) Inventors: Robert Eastlack, San Diego, CA (US); James Bruffey, San Diego, CA (US); Maneesh Bawa, San Diego, CA (US); Brian Bowman, Carlsbad, CA (US); Benjamin Arnold, San Diego, CA (US); Jude Paganelli, Coronado, CA (US)

(73) Assignee: Spine Innovation, LLC, Del Mar, CA (US)

( * ) Notice: Subject to any disclaimer, the term of this patent is extended or adjusted under 35 U.S.C. 154(b) by 89 days.

(21) Appl. No.: 16/949,132

(22) Filed: Oct. 15, 2020

(65) Prior Publication Data

US 2021/0022886 A1    Jan. 28, 2021

Related U.S. Application Data

(63) Continuation of application No. 15/870,397, filed on Jan. 12, 2018, now abandoned, which is a
(Continued)

(51) Int. Cl.
*A61F 2/46* (2006.01)
*A61B 17/02* (2006.01)
(Continued)

(52) U.S. Cl.
CPC .......... *A61F 2/4611* (2013.01); *A61B 17/025* (2013.01); *A61F 2/4455* (2013.01);
(Continued)

(58) Field of Classification Search
CPC ...... A61F 2/4611; A61F 2/4455; A61F 2/447; A61F 2/4603; A61F 2002/30235;
(Continued)

(56) References Cited

U.S. PATENT DOCUMENTS 3,486,505 A   12/1969 Gordon
5,431,658 A *  7/1995 Moskovich .......... A61B 17/025
                                                    606/90
(Continued)

FOREIGN PATENT DOCUMENTS

WO    WO-2015003172 A1    1/2015

OTHER PUBLICATIONS

European search report with written opinion dated Feb. 24, 2017 for EP14820002.
(Continued)

*Primary Examiner* — Jessica Weiss
(74) *Attorney, Agent, or Firm* — Acuity IP, LLC; Nathan S. Cassell

(57) ABSTRACT

A delivery instrument for placing an interbody implant into an intervertebral space of a patient comprises a plurality of elongated plates disposed adjacent one another. Each elongated plate has a proximal portion and a distal portion. The distal portion is sized and shaped to fit into the intervertebral space, and is configured to engage a vertebral body in the intervertebral space. An expandable member is coupled to the plurality of elongated plates so as to form an enclosed tube that is sized and shaped to receive the interbody implant. The expandable member allows for translation of the plurality of elongated plates relative to one another as the interbody implant passes through the tube.

10 Claims, 27 Drawing Sheets

Related U.S. Application Data continuation of application No. 15/206,179, filed on Jul. 8, 2016, now Pat. No. 9,901,464, which is a continuation of application No. 14/322,589, filed on Jul. 2, 2014, now Pat. No. 9,408,721.

(60) Provisional application No. 61/842,879, filed on Jul. 3, 2013.

(51) Int. Cl.
*A61F 2/44* (2006.01)
*A61F 2/30* (2006.01)

(52) U.S. Cl.
CPC ....... *A61B 2017/0256* (2013.01); *A61F 2/447* (2013.01); *A61F 2/4603* (2013.01); *A61F 2002/30235* (2013.01); *A61F 2002/30563* (2013.01); *A61F 2002/30579* (2013.01); *A61F 2002/30594* (2013.01); *A61F 2002/4615* (2013.01); *A61F 2002/4628* (2013.01)

(58) Field of Classification Search
CPC .. A61F 2002/30563; A61F 2002/30579; A61F 2002/30594; A61F 2002/4615; A61F 2002/4628; A61B 17/025; A61B 2017/0256
USPC .............................. 606/99–100, 86 A, 86 B; 623/17.11–17.16; 600/203
See application file for complete search history.

(56) References Cited

U.S. PATENT DOCUMENTS

| | | | |
|---|---|---|---|
| 6,652,533 B2 | 11/2003 | O'Neil | |
| 6,755,841 B2 | 6/2004 | Fraser et al. | |
| 7,063,664 B2 | 6/2006 | Mohajer | |
| 7,625,379 B2 | 12/2009 | Puno et al. | |
| 7,896,884 B2 | 3/2011 | Wing et al. | |
| RE43,317 E | 4/2012 | Fraser et al. | |
| 8,343,163 B1 | 1/2013 | Arambula et al. | |
| 8,439,924 B1 | 5/2013 | Mcbride et al. | |
| 8,679,184 B2 | 3/2014 | Kube, II | |
| 8,864,770 B2* | 10/2014 | Blain | A61F 2/4455 606/86 A |
| 9,211,140 B2 | 12/2015 | Lauryssen et al. | |
| 9,358,124 B2* | 6/2016 | Davenport | A61F 2/4465 623/17.11 |
| 9,408,721 B2 | 8/2016 | Eastlack et al. | |
| 9,474,629 B2 | 10/2016 | Jiang et al. | |
| 9,901,464 B2 | 2/2018 | Eastlack et al. | |
| 2004/0267277 A1 | 12/2004 | Zannis et al. | |
| 2005/0192482 A1* | 9/2005 | Carpenter | A61B 1/00142 600/203 |
| 2007/0021656 A1* | 1/2007 | Martin | A61B 17/02 600/231 |
| 2009/0005784 A1* | 1/2009 | Blain | A61B 17/025 606/86 A |
| 2009/0048604 A1 | 2/2009 | Milz et al. | |
| 2009/0281551 A1* | 11/2009 | Frey | A61B 17/025 606/90 |
| 2010/0023013 A1 | 1/2010 | Flickinger et al. | |
| 2010/0076502 A1* | 3/2010 | Guyer | A61B 17/34 600/184 |
| 2011/0071634 A1* | 3/2011 | Jiang | A61F 2/4465 623/17.11 |
| 2011/0301424 A1* | 12/2011 | Steigerwald | A61B 1/303 600/235 |
| 2012/0016196 A1 | 1/2012 | Kambin et al. | |
| 2012/0253412 A1 | 10/2012 | Lee et al. | |
| 2015/0012098 A1 | 1/2015 | Eastlack et al. | |
| 2015/0080973 A1 | 3/2015 | Eastlack et al. | |
| 2016/0058578 A1* | 3/2016 | Lauryssen | A61F 2/4455 606/86 A |
| 2019/0240044 A1* | 8/2019 | Shinbrot | A61F 2/4611 623/17.11 |

OTHER PUBLICATIONS

International search report and written opinion dated Nov. 4, 2014 for PCT Application No. US2014/045489.
Notice of allowance dated Apr. 15, 2016 for U.S. Appl. No. 14/322,589.
Notice of Allowance dated Oct. 12, 2017 for U.S. Appl. No. 15/206,179.
Office action dated Jan. 12, 2016 for U.S. Appl. No. 14/322,589.
Office action dated May 22, 2017 for U.S. Appl. No. 15/206,179.
Office action dated Sep. 28, 2015 for U.S. Appl. No. 14/322,589.

* cited by examiner

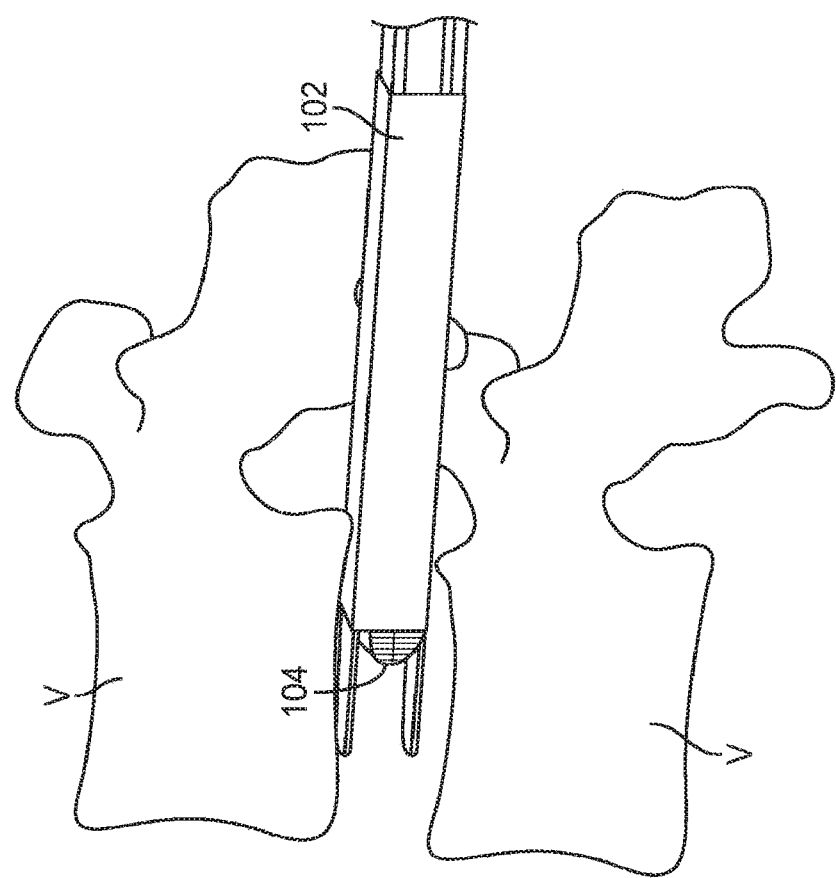

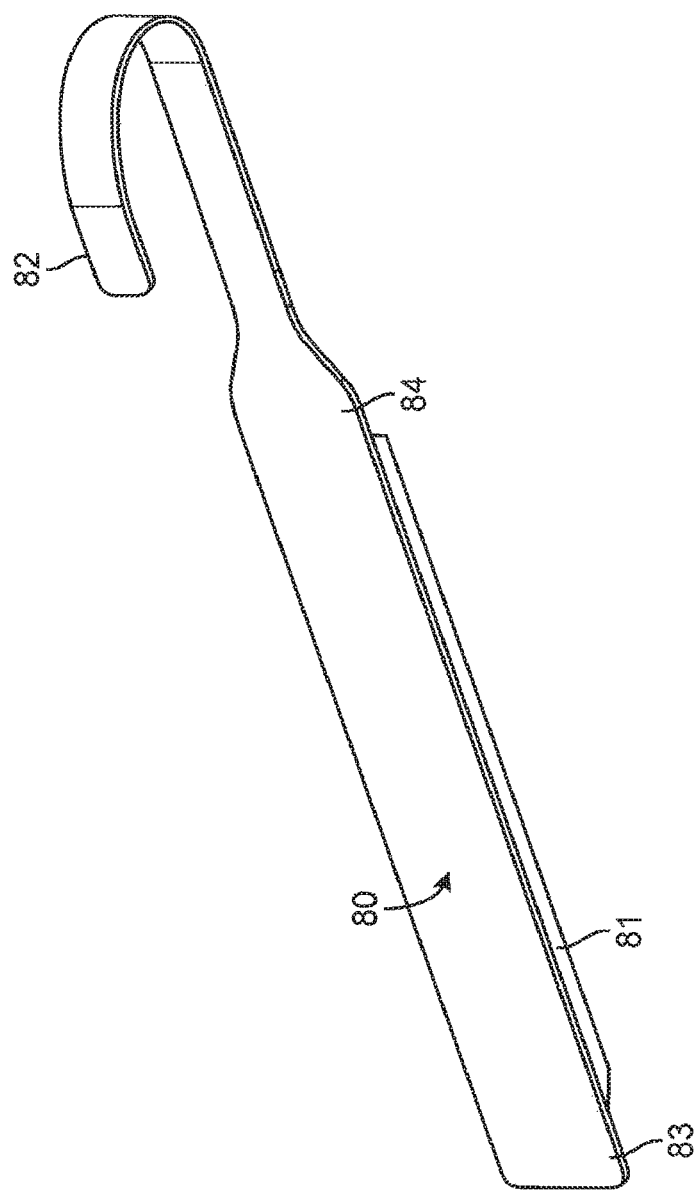

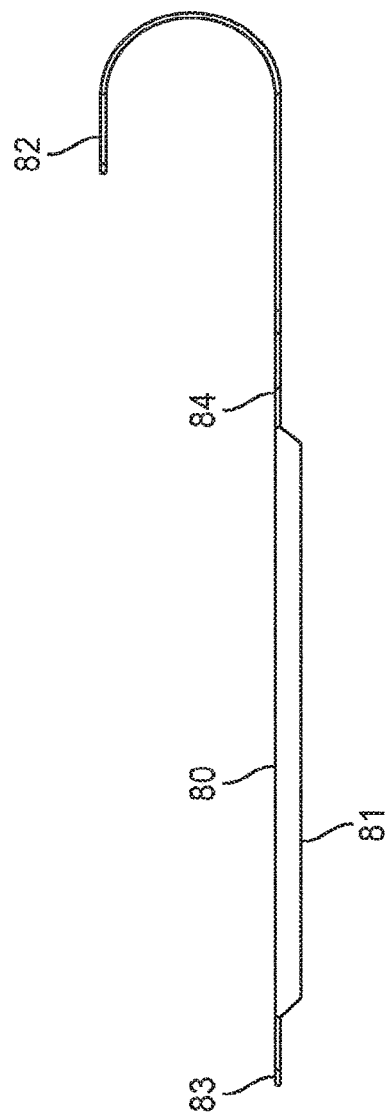

METHODS AND APPARATUS FOR AN INSERTION GUIDE DEVICE

CROSS-REFERENCE

The present application is a continuation of U.S. patent application Ser. No. 15/870,397, filed Jan. 12, 2018, which is a continuation of U.S. patent application Ser. No. 15/206,179, filed Jul. 8, 2016, now U.S. Pat. No. 9,901,464, which is a continuation of U.S. patent application Ser. No. 14/322,589, filed Jul. 2, 2014, now U.S. Pat. No. 9,408,721, which is a non-provisional of, and claims the benefit of U.S. Provisional Patent Application No. 61/842,879 filed on Jul. 3, 2013; the entire contents of which are incorporated herein by reference.

The present application is related to U.S. patent application Ser. No. 14/322,702 filed the same day as the present application; the entire contents of which are incorporated herein by reference.

BACKGROUND OF THE INVENTION

1. Field of the Invention

The present invention generally relates to medical devices and methods, and more particularly relates to delivery instruments and methods for deploying an interbody fusion implant into an intervertebral disc space.

Various interbody fusion implants (also referred to as interbody fusion devices) may be implanted in the intervertebral disc space. These devices facilitate fusion of the adjacent vertebrae together. Depending on the size of the interbody fusion device and the corresponding delivery instrument, a surgeon may have to remove bone from the surrounding vertebrae in order to provide adequate space. Clearly, it would be desirable if bone removal could be minimized or eliminated all together. Moreover, adjacent tissue may also need to be retracted or removed, and it would be desirable to minimize or eliminate this as well. Also, insertion of the implant often requires distraction of the vertebrae, therefore it would be desirable to provide a low profile implant that minimizes the amount of distraction required.

Newer interbody fusion devices are being developed which have a smaller more compact profile for delivery and a larger expanded profile after deployment. The smaller delivery size facilitates delivery, and the larger deployed configuration facilitates support and fusion of the bone. Therefore, it would be desirable to provide improved delivery instruments which can accurately and safely deliver and deploy interbody fusion devices including those that have collapsed configurations for delivery and expanded configurations after deployment. At least some of these objectives will be satisfied by the devices and methods disclosed below.

2. Description of the Background Art

The following U.S. patents and U.S. patent publications are related to interbody fusion devices and their delivery: U.S. Pat. Nos. 6,652,533; 3,486,505; 2011/0071634; 7,896,884; 7,625,379; 6,755,841; 5,431,658; and RE43317.

SUMMARY OF THE INVENTION

The present invention generally relates to medical devices and methods, and more particularly relates to delivery instruments and methods for deploying an interbody fusion implant into an intervertebral disc space.

In a first aspect of the present invention, a delivery instrument for facilitating the placement of an interbody implant into an intervertebral space of a patient comprises a plurality of elongated plates disposed adjacent one another. Each elongated plate has a proximal portion and a distal portion. The distal portion of each elongated plate is sized and shaped to fit into the intervertebral space, and also the distal portion of each elongated plate is configured to engage a vertebral body in the intervertebral space. An expandable member is coupled to the plurality of elongated plates so as to form an enclosed tube for at least a portion of the length of the plurality of elongated plates. The enclosed tube is sized and shaped to receive the interbody implant. The expandable member allows for translation of the plurality of elongated plates relative to one another as the interbody implant passes through the tube.

The expandable member may be an elastomeric tube that is disposed over the plurality of elongated plates. The expandable member may comprise two or more flexible sheets of resilient material that extend from one elongated plate to another elongated plate. The plurality of elongated plates may have a geometry that is configured to engage the interbody implant passing through the tube, and the plurality of elongated plates may have a geometry that guides the interbody implant into the intervertebral space. The geometry that engages the interbody implant may comprise a plurality of rails extending from the plurality of elongated plates.

The plurality of elongated plates may be expandable to allow the delivery instrument to expand in one or multiple directions in order to accommodate various sizes of interbody implants. The plurality of elongated plates may have a longitudinally oriented slit located therealong, and the slit may be configured to allow the plurality of plates to expand and contract. The longitudinally oriented slit may comprise a stress relief feature. The plurality of plates may be coupled together adjacent their proximal portion.

At least one of the plurality of elongated plates may comprise a finger loop adjacent a proximal end thereof, and the finger loop may be configured to facilitate grasping by an operator's finger. The delivery instrument may further comprise a stop element disposed adjacent a distal portion of at least one of the plurality of elongated plates. The stop element may be configured to limit insertion of the delivery instrument into the intervertebral space.

In another aspect of the present invention, a system for delivering an implant to an intervertebral space of a patient comprises the delivery instrument previously described above as well as an interbody implant.

In still another aspect of the present invention, a method for delivering an interbody implant into an intervertebral space between adjacent vertebral bodies of a patient comprises providing a delivery instrument having a plurality of elongated plates disposed adjacent one another and coupled together with an expandable member, and advancing the interbody implant along a tube formed by the plurality of elongated plates and the expandable member. The method also comprises translating the plurality of elongated plates relative to one another as the interbody implant advances along the tube, ejecting the interbody implant from the delivery device, and returning the elongated plates to an unbiased configuration after the interbody implant has been ejected.

Translating the plurality of elongated plates may comprise moving the plurality of plates away from one another, or expanding or collapsing the expandable member. The expandable member may comprise an elastomeric tube that is disposed over the plurality of elongated plates.

Advancing the interbody implant may comprise guiding the interbody implant along the tube with a plurality rails extending from the plurality of elongated plates. A stress relief feature may be included in one or more of the plurality of elongated plates, and the method may further comprise relieving stress in the delivery instrument as the interbody implant is translated therealong.

Translating the plurality of elongated plates may comprise expanding or contracting a slit disposed in at least one of the plurality of elongated plates. The plurality of elongated plates may be coupled to one another adjacent a proximal portion thereof, and translating the plurality of elongated plates may comprise pivoting the plurality of elongated plates relative to the proximal portion. Ejecting may comprise disposing the interbody implant in the intervertebral space. The method may further comprise engaging a distal portion of the plurality of elongated plates with the vertebral bodies.

The method may further comprise grasping the delivery device by inserting one or more fingers in a finger loop disposed on a proximal portion of at least one of the plurality of elongated plates. The method may also further comprise advancing the plurality of elongate plates into the intervertebral space, and limiting penetration of the plurality of elongate plates into the intervertebral space. This may be accomplished by engaging a stop element disposed on at least one of the plurality of elongate plates against an edge of at least one of the adjacent vertebral bodies.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 10A-10F illustrate insertion of the insertion guide device into the intervertebral disc space and delivery of an interbody implant.

FIG. 12A illustrates a perspective view of another exemplary embodiment of an elongated plate used in an insertion guide device.

FIG. 12B is a side view of FIG. 12A.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1:
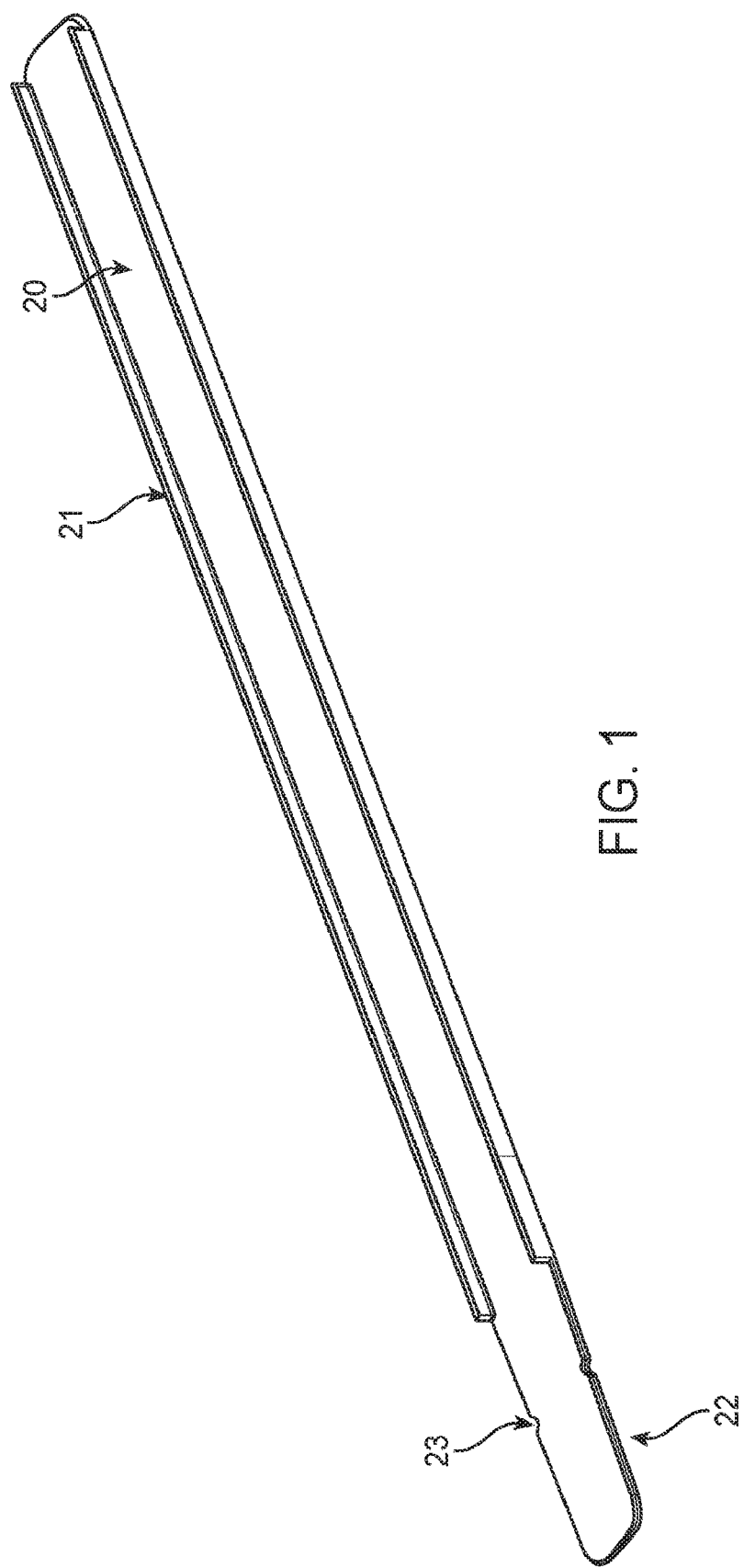
FIG. 1 is a perspective view of an elongated plate component.

FIG. 1 shows the elongated plate 20 with optional rails 21 extending outward from the elongated plate, to guide the implant into the disc space. The rails 21 extend up to the distal portion 22 of the elongated plate 20 that enters the disc space. The rails 21 end prior to the distal portion 22 of the elongated plate 20 in order to decrease the width of the elongated plate 20 that has to pass by the neural elements and into the disc space. The rails 21 are set at a distance apart to match the width of the implant being passed through it further optimizing the width of the elongated plate 20 so that it is as narrow as possible (low profile) as it passes by the neural elements. Notch 23, is an optional feature in the elongated plate 20 to allow for the engagement of the expandable member 30. This notch 23 prevents the axial migration of the expandable member 30 along the length of the elongated member 20. The elongated plate 20 may be made out of a variety of materials including, but not limited to, metals such as stainless steel or aluminum, carbon fiber, other composite materials, polymers such ABS, and Radel™.

Figure 2:
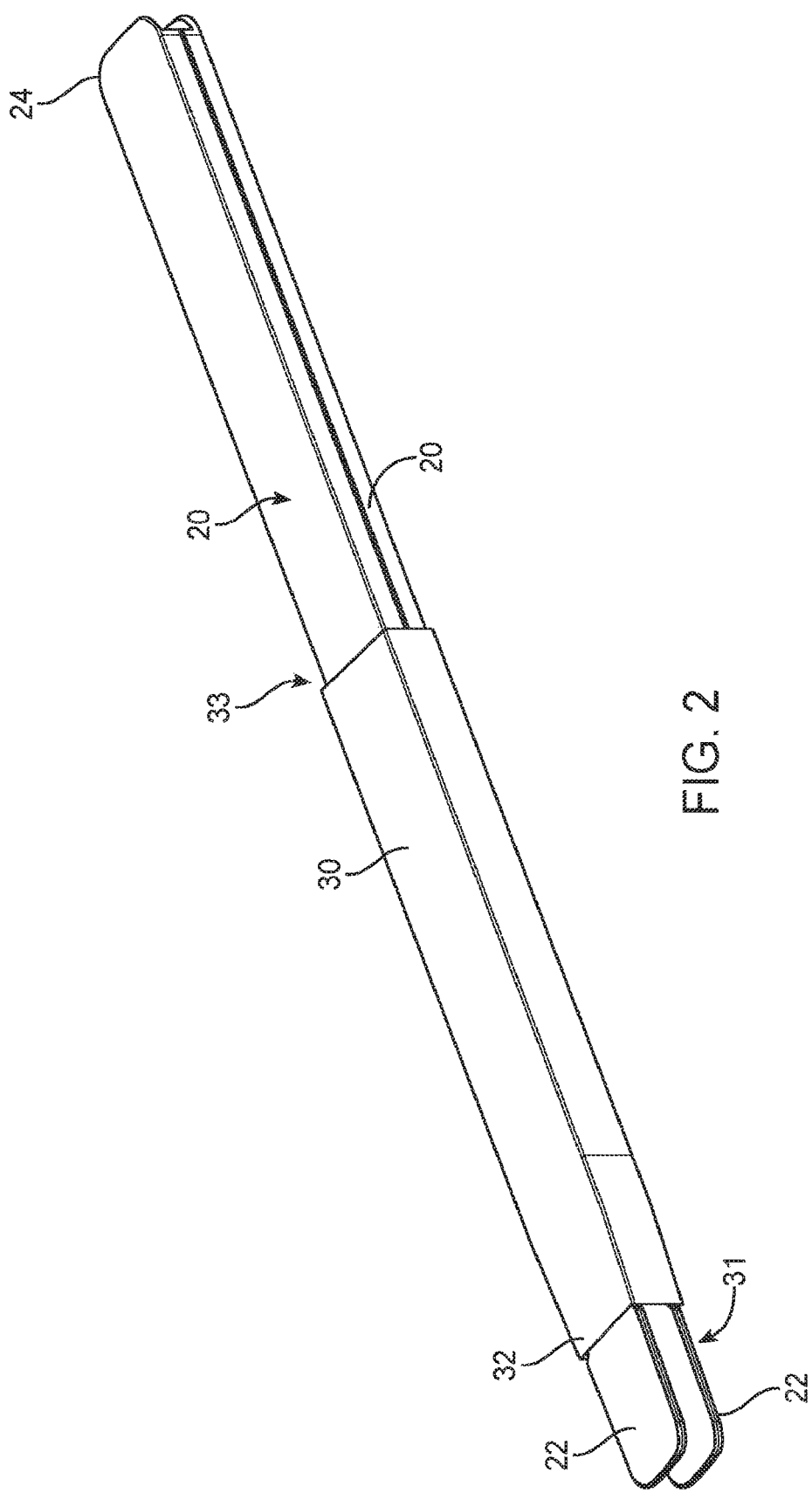
FIG. 2 is a perspective view of an insertion guide device, using the elongated plate in FIG. 1, in the collapsed state.

Two of the elongated plates 20 are shown in FIG. 2 joined by an expandable member 30 in one exemplary embodiment of the device. In this configuration the distal portion of the device 31 that enters the disc space is in a collapsed configuration with each distal portion 22 of the elongated plates 20 adjacent or engaged with one another and being positioned such that they can engage the endplates of the adjacent vertebral bodies in a collapsed disc space. In this embodiment the expandable member 30 has a distal end 32 that doesn't enter into the disc space, in addition, the proximal end 33 of the expandable member 30 does not extend to the proximal end 24 of the elongated member 20. The expandable member 30 may be made of a variety of different materials including, but not limited to, polyurethane, polyisoprene, and latex.

Figure 3:
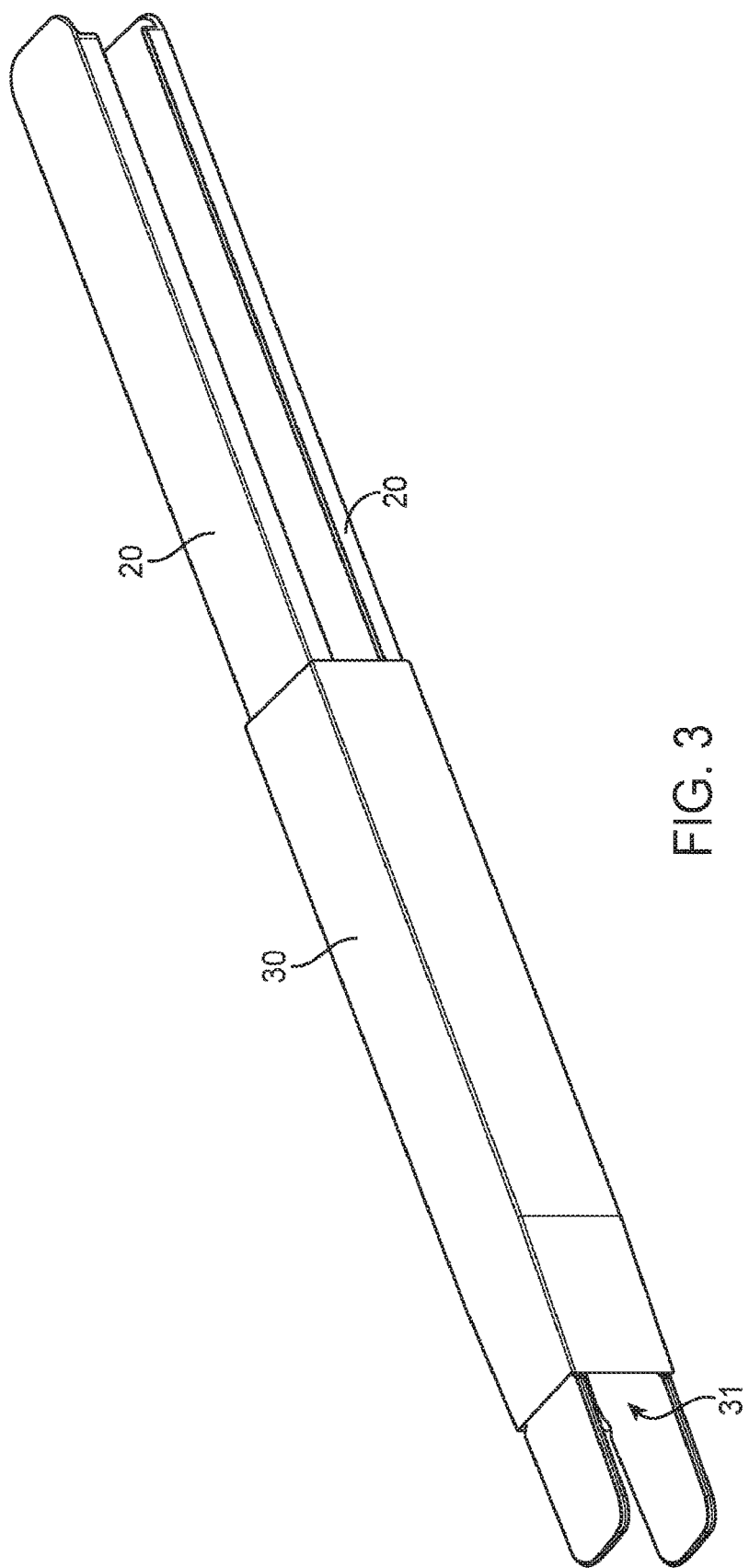
FIG. 3 is a perspective view of the insertion guide device in FIG. 2 in an expanded state.

In FIG. 3, the device is shown in an expanded state with the distal end of the device 31 aiding in distraction of the disc space and the expandable member 30 being stretched to accommodate the increased distance between the elongated plates 20. The distal ends of elongated members 20 are separated from one another by a gap and displaced apart relative to the collapsed configuration.

Figure 4:
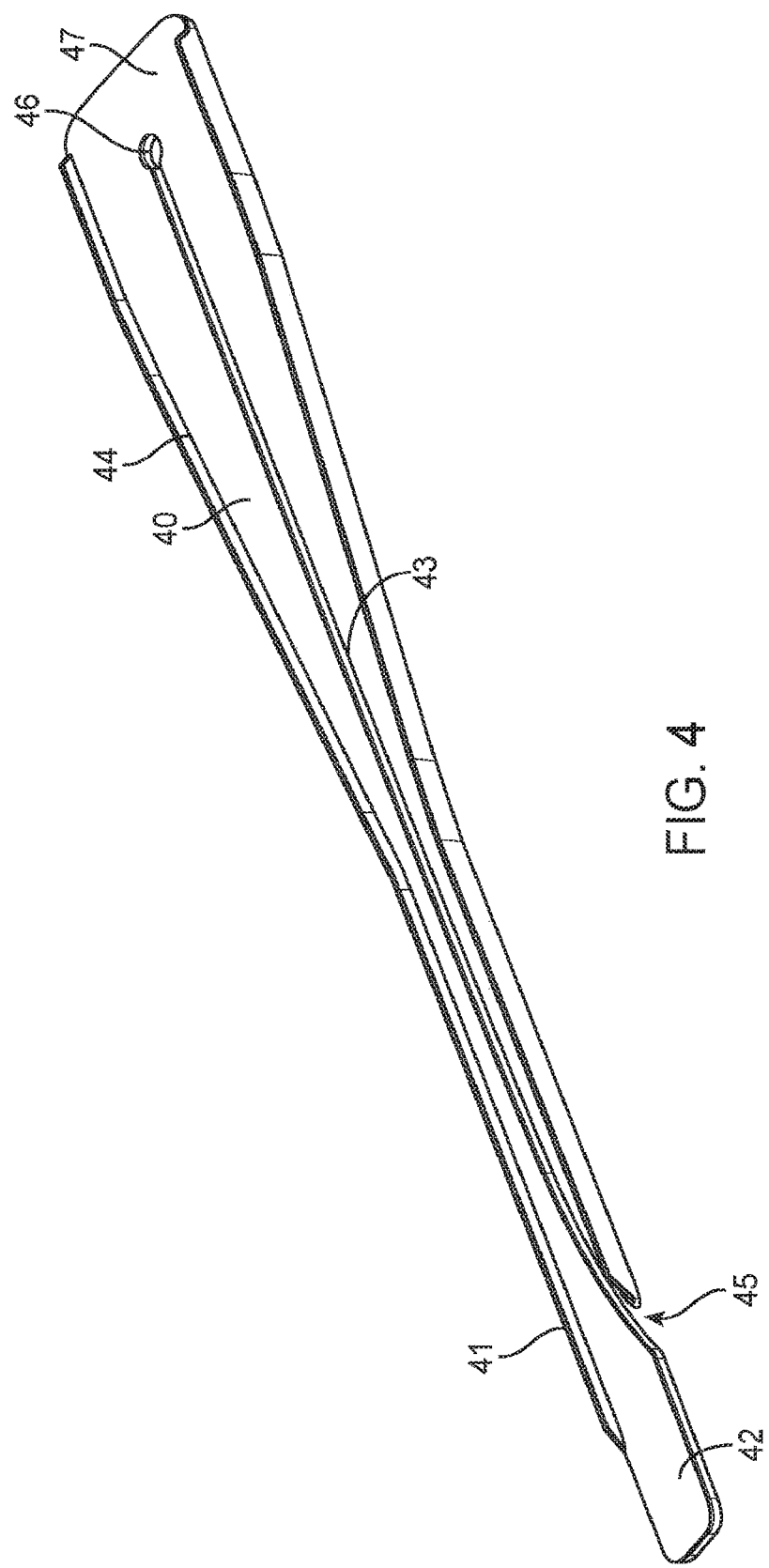
FIG. 4 is a perspective view of an elongated plate component.

FIG. 4 shows another exemplary embodiment of the elongated plate 40. In this iteration there are rails 41 extending outward from the plate 40 and that run the length of the elongated plate 40 terminating only where the distal end 42 enters the disc space. The major addition in this embodiment of the design is the ability of the elongated plate 40 to expand to accommodate varying width implants. This expansion is accommodated by the split or slot 43 in the elongated plate 40 that runs from the proximal end 47 to the distal end 42. The split 43 runs out of the lateral edge 45 of the elongated plate 40 allowing for a solid surface within the disc space at the distal end 42 for better distraction of the disc space and a decreased potential for subsidence of the elongated plate 40 into the endplate. The rails 41 have a tapered portion 44 that allow for the insertion of a wide implant at the proximal end 47 prior to the expansion of the elongated plate 40. Additionally, the split 43 in the elongated plate 40 has a stress relief cut 46 near the proximal end 47. In this embodiment, the stress relief 46 is a circular through hole in the elongated plate. This version of the elongated plate 40 is shown as part of an assembled device in FIG. 5. In this embodiment of the device, two elongated plates 40 are joined by the expandable member 50.

Figure 5:
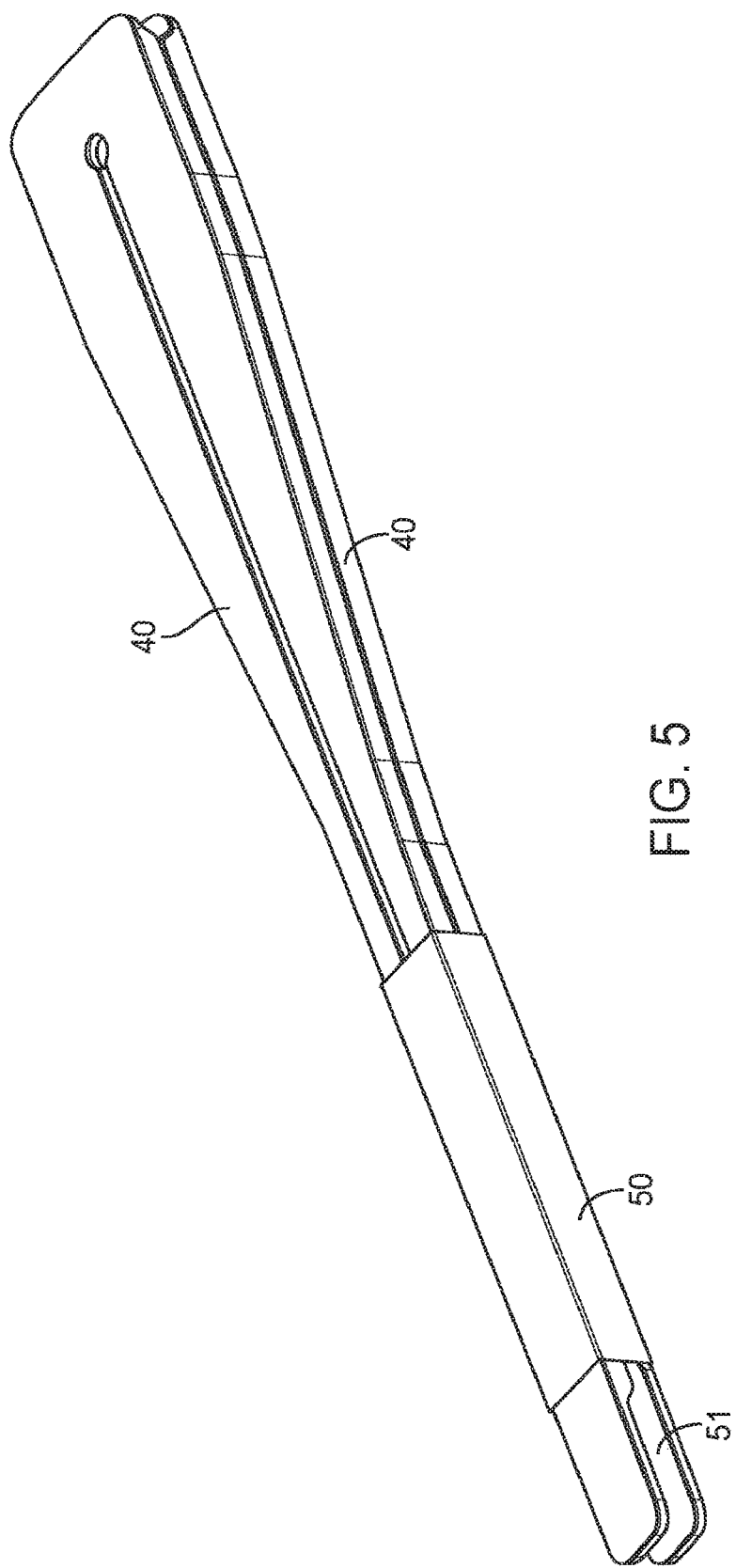
FIG. 5 is a perspective view of an insertion guide device, using the elongated plate in FIG. 4, in the collapsed state.
Figure 6:
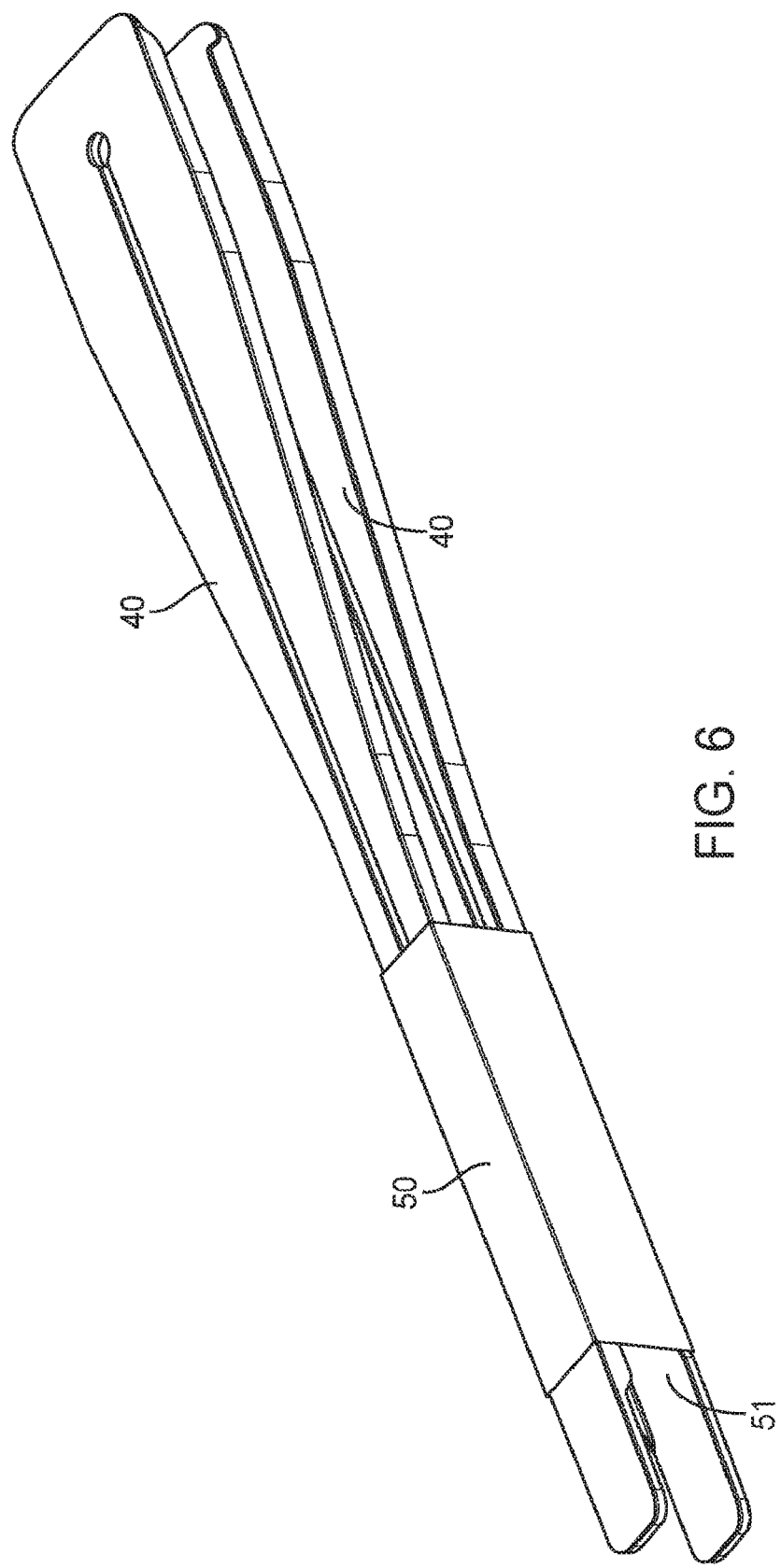
FIG. 6 is a perspective view of the insertion guide device in FIG. 5 in an expanded state.

FIG. 5 shows the device in its collapsed state with the little distance between the elongated plates 40 at the distal end of the device 51. This same embodiment of the device is shown in FIG. 6 in an expanded state with a distracted distal end of the construct 51. The top elongated plate is substantially the same as the bottom elongated plate.

Figure 7:
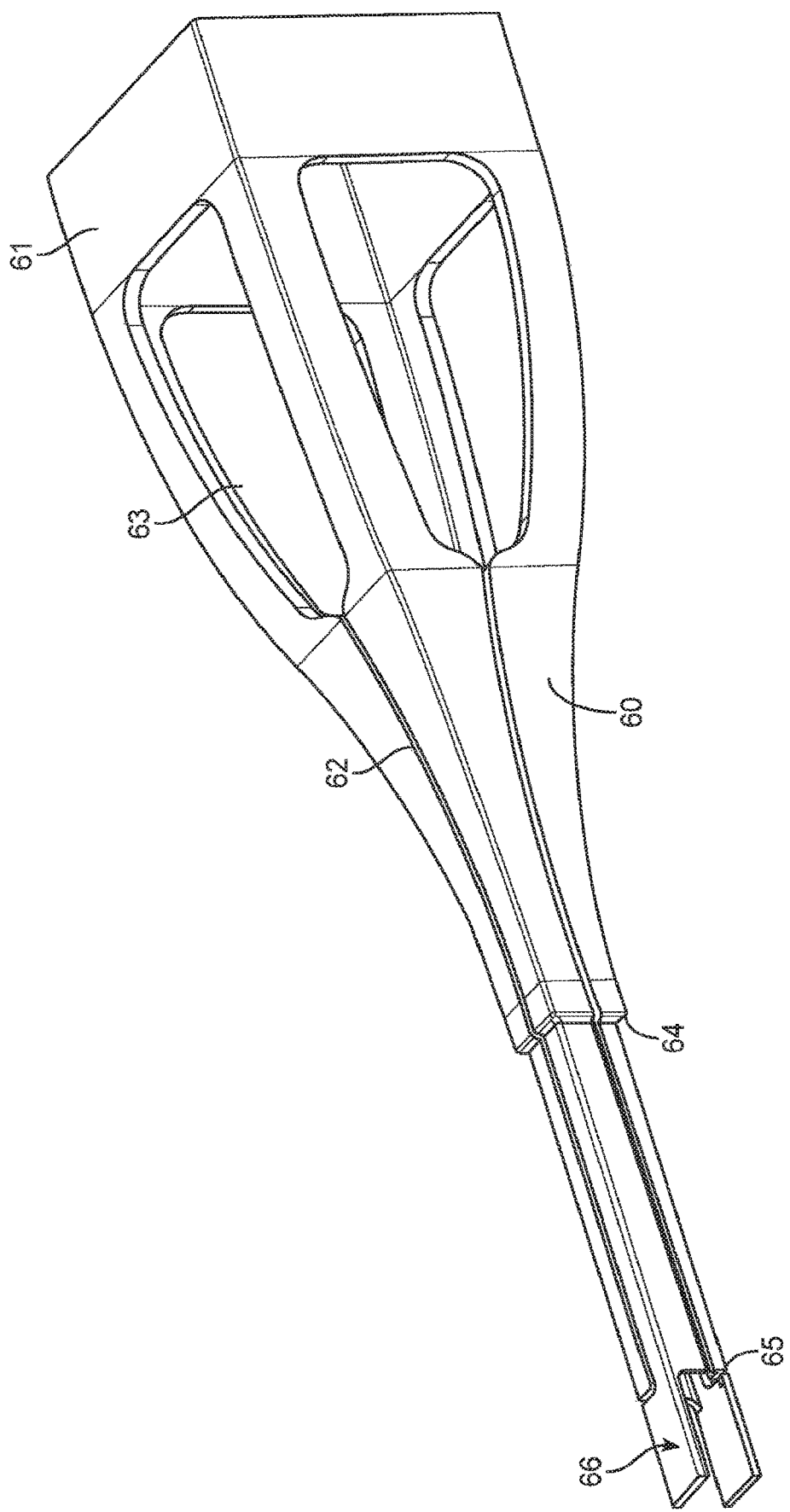
FIG. 7 is a perspective view of an elongated plate component.

FIG. 7 shows another preferred embodiment of the elongated plate 60. In this embodiment, the elongated plates are joined at the proximal end 61. Similar to the previous embodiment 40, this embodiment has a split 62 or slot to allow for expansion in width, a tapered portion 60, a lateral run out 65 of the split 62, and a flat surface that contacts the vertebral end plates at the distal end 66. This embodiment of the elongated plate 60 also has a step 64 to help constrain the expanding member 70 as seen in FIG. 8.

Figure 8:
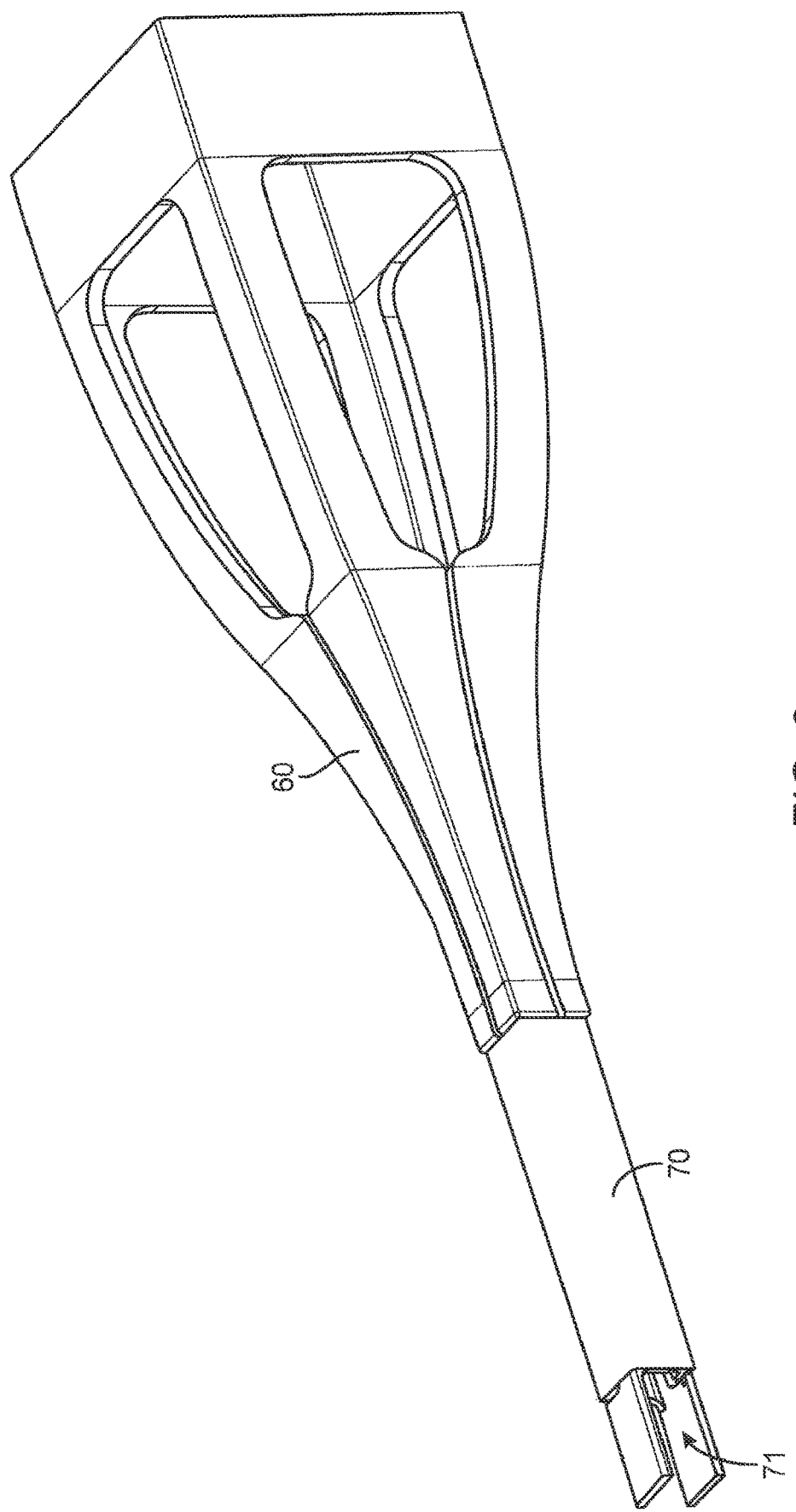
FIG. 8 is a perspective view of an insertion guide device, using the elongated plate in FIG. 7, in the collapsed state.

FIG. 8 shows the embodiment of the elongated plate 60 with the expanding member 70 covering the distal portion of the device to protect the neural elements and terminating just prior to the distal end of the device 71 that enters the disc space.

Figure 9:
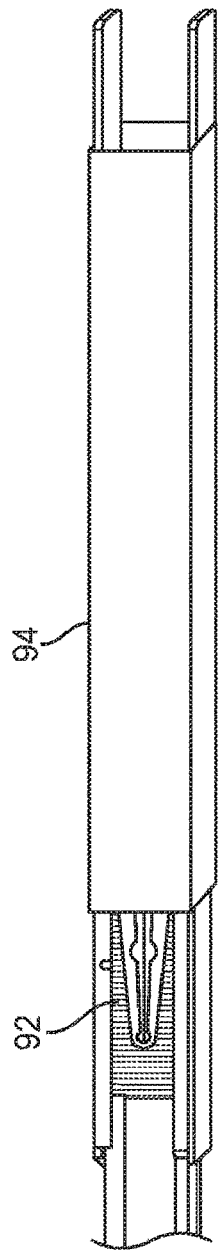
FIG. 9 illustrates an interbody implant coupled to the insertion guide device.

FIG. 9 illustrates an interbody implant 92 coupled to the insertion guide device 94. The interbody implant is in its collapsed configuration, and it may be any of the embodiments disclosed herein, or disclosed in U.S. patent application Ser. No. 14/322,702 filed the same day as the present application and previously incorporated herein by reference. The insertion guide device may be any of the embodiments disclosed in this specification.

Figure 10A:
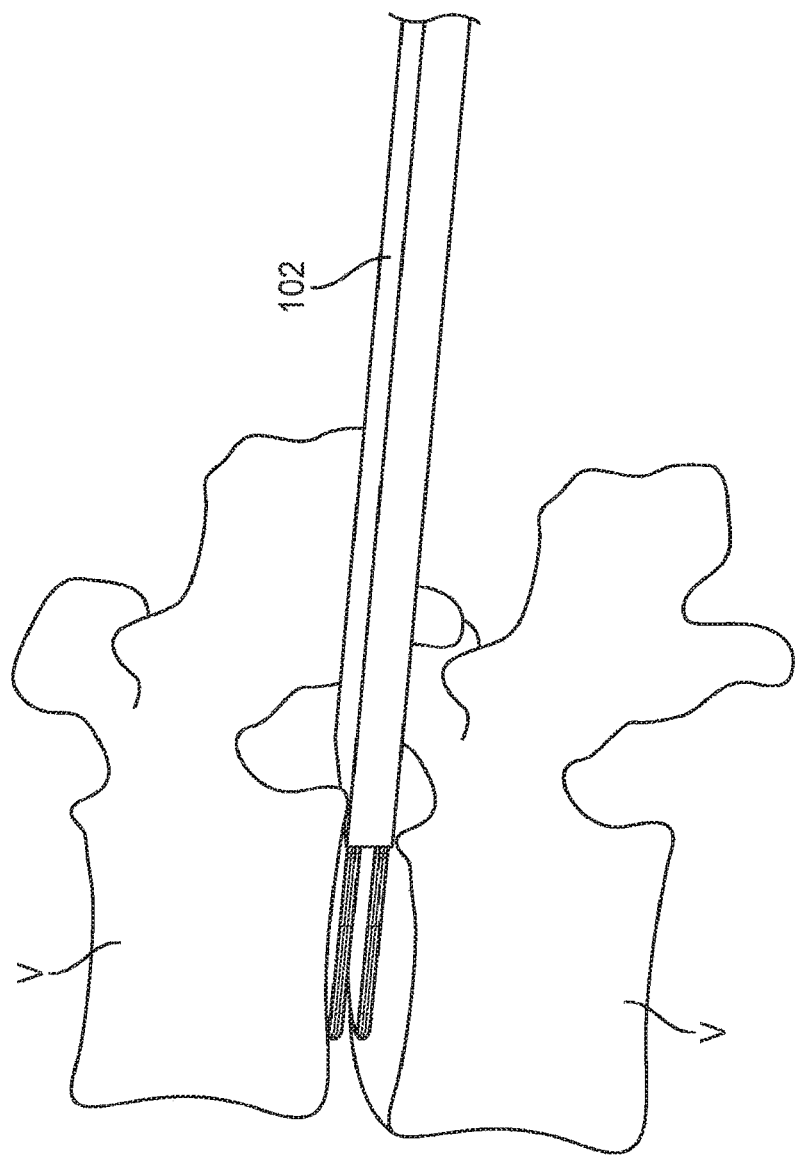

FIGS. 10A-10F illustrate an exemplary method of delivering an interbody implant using an insertion guide device such as those described in this specification. In FIG. 10A, the insertion guide device 102 is inserted into the intervertebral disc space between adjacent vertebrae V. The elongated plates are in their collapsed configuration. The expandable member is advanced toward the vertebrae, but is not inserted into the intervertebral space.

Figure 10C:
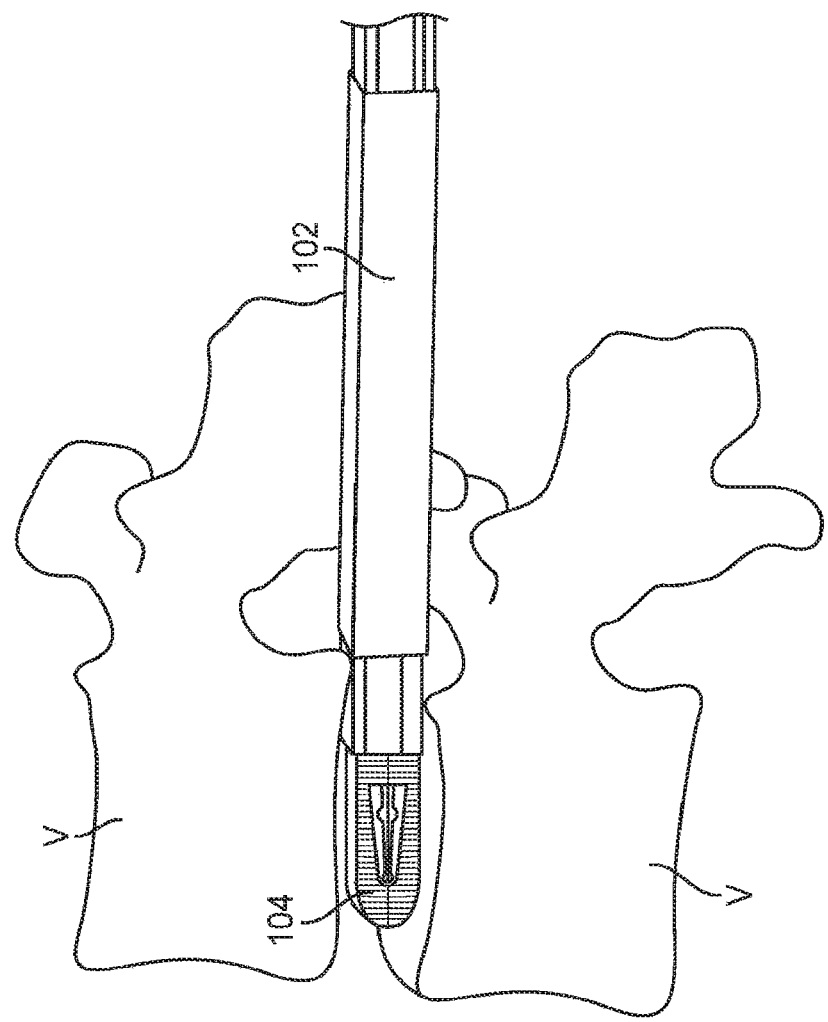
Figure 10D:
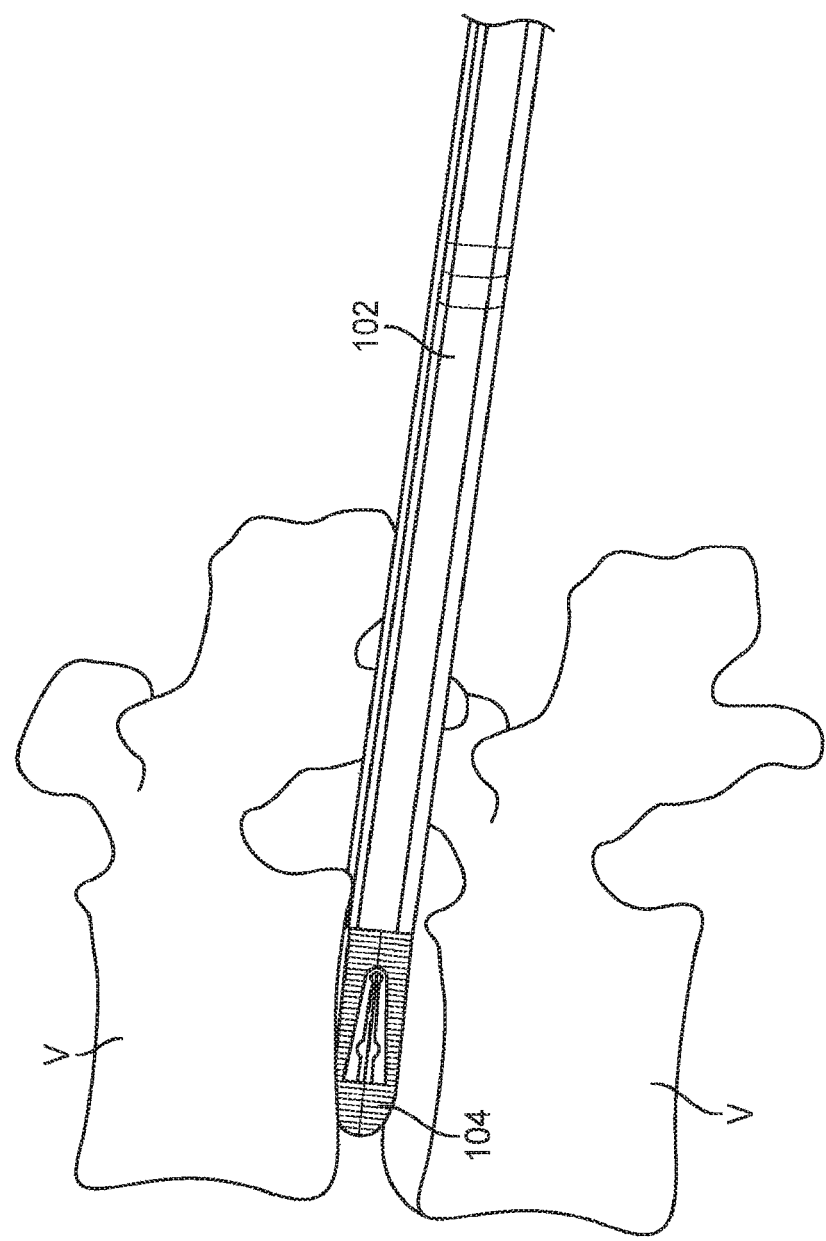
Figure 10E:
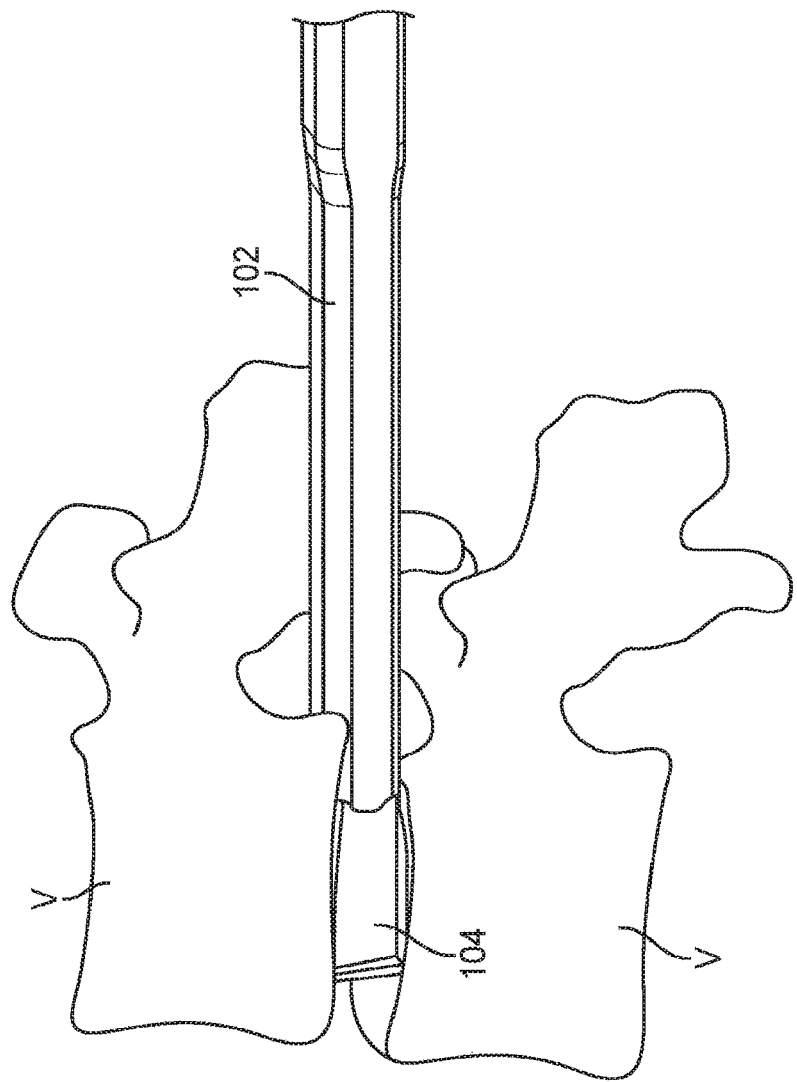
Figure 10F:
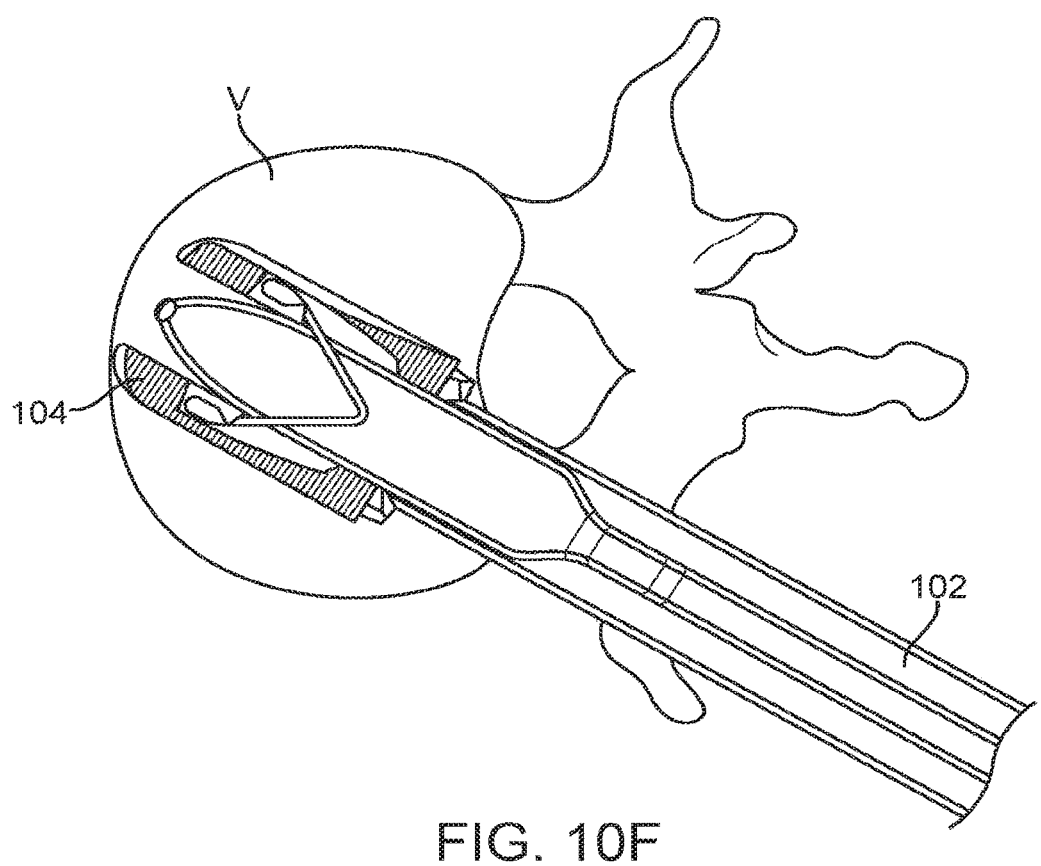

In FIG. 10B, the interbody implant 104 is advanced distally out of the insertion guide device 102 until it is exposed from the expandable portion of the insertion guide device and positioned in a desired location between the vertebrae, as illustrated in FIG. 10C. FIG. 10D is similar to FIG. 10C but illustrates a longer portion of the insertion guide device. In FIG. 10E, the interbody implant and the insertion guide device have been rotated preferably 90 degrees so that the textured surfaces of the interbody implant are in engagement with the endplates of the vertebrae. FIG. 10F is a top view of the interbody implant and insertion guide device with the upper vertebra removed for ease in viewing. Additionally, the interbody implant has been laterally expanded to increase its width. The interbody implant and the insertion guide device may be any of the embodiments disclosed herein. Additional details on the interbody implant are disclosed in U.S. patent application Ser. No. 14/322,702 filed the same day as the present application, and previously incorporated herein by reference.

Figure 11A:
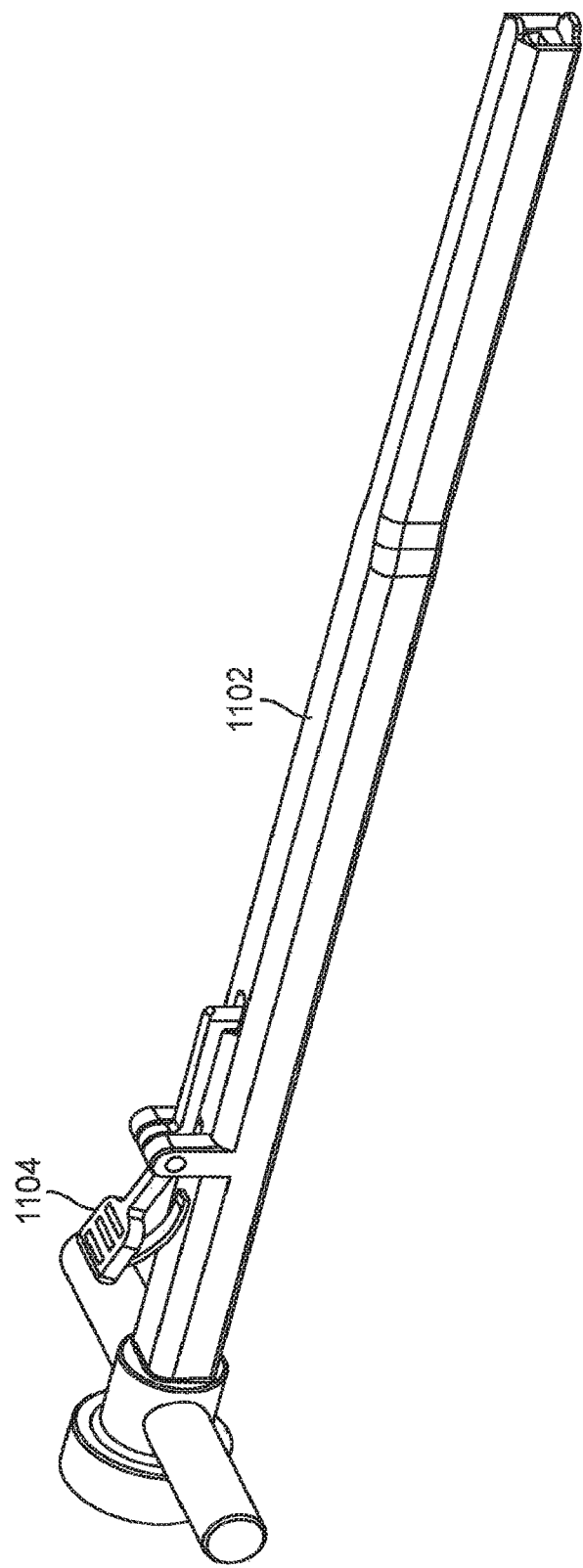
FIGS. 11A-11B illustrate a pusher element for pushing an interbody implant from the insertion guide device.
Figure 11B:
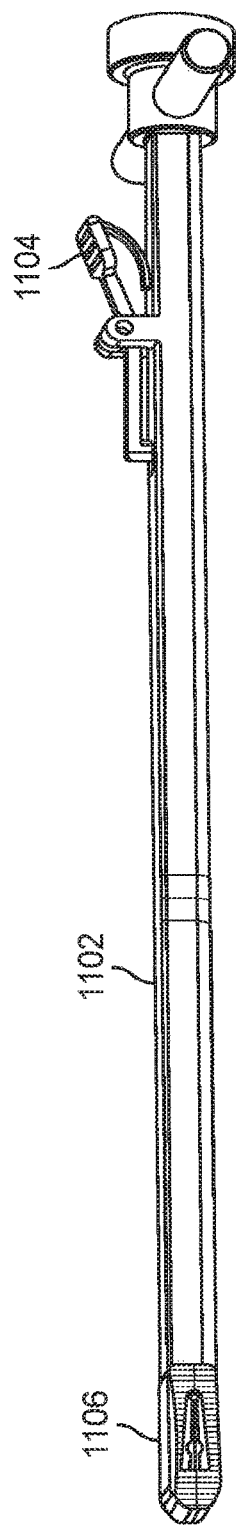

FIGS. 11A-11B illustrate the pusher element which may be advanced or retracted by an operator to move the interbody implant through the insertion guide device disclosed above. In FIG. 11A, the pusher element 1102 includes an elongate shaft with a handle on the proximal end for ease in manipulation. A lever 1104 helps lock the pusher to the interbody implant. FIG. 11B illustrates the interbody implant 1106 coupled to the pusher element 1102. A leaf spring is disposed under the actuation lever thereby biasing the lever in the up position so that the pusher remains locked with the interbody implant. When the lever is moved, the implant may be decoupled from the pusher. The pusher/implant assembly is preferably inserted into the elongated plate assembly for delivery to the intervertebral space.

FIGS. 12A-12B illustrate another exemplary embodiment of elongated plates that may be used in an insertion guide device. FIG. 12A shows an exemplary embodiment of an elongated plate 80 with rails 81 that extend outward from the plate and guide the implant into the disc space. Pre-formed finger loops 82 on the proximal end of the plate allow a user to more easily control the insertion guide device position. Rails 81 end prior to the distal portion 83 of the elongated plate and extend up to the transition 84 to finger loop 82. FIG. 12B illustrates a side view of FIG. 12A.

Figure 13A:
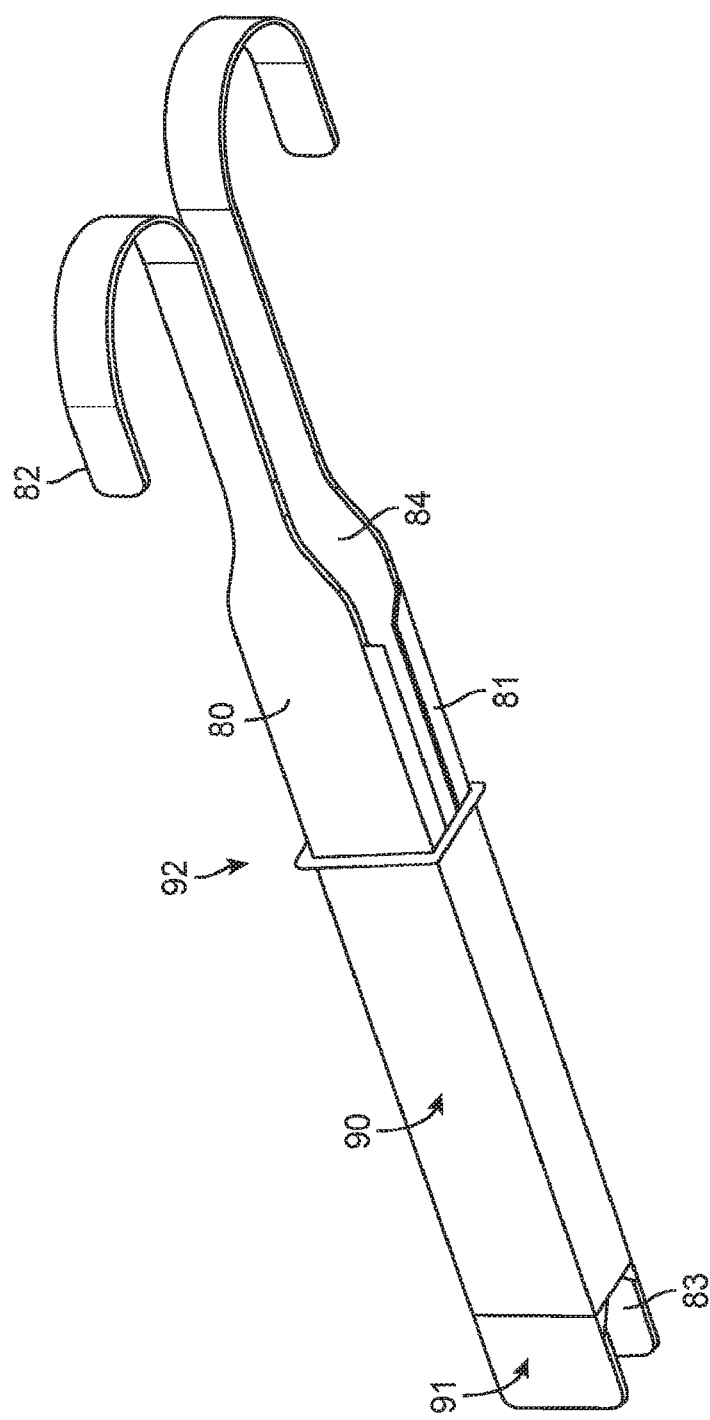
FIG. 13A illustrates a perspective view of an insertion guide device using the elongated plate in FIG. 12A and in the collapsed configuration.
Figure 13B:
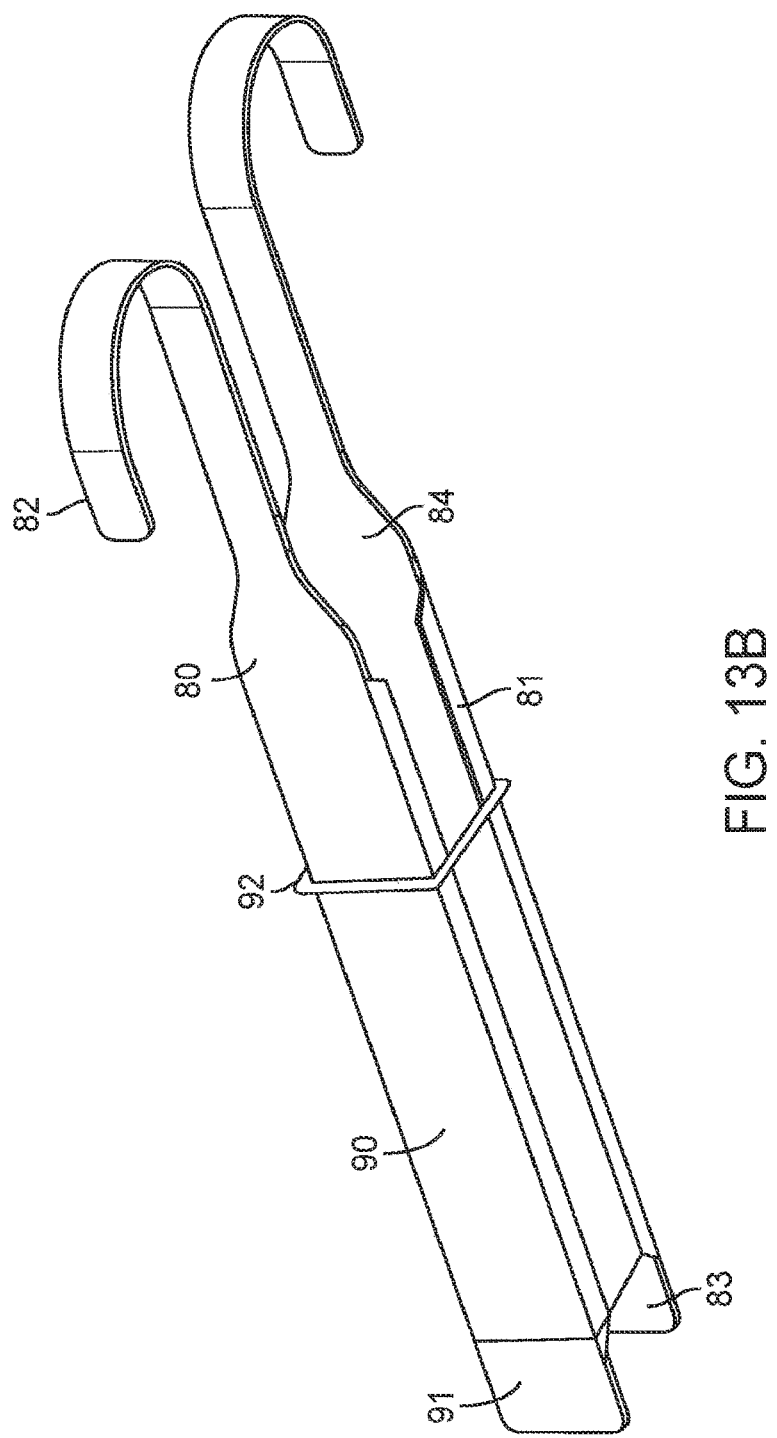
FIG. 13B illustrates the embodiment of FIG. 13A in the expanded configuration.

FIGS. 13A-13B illustrate an insertion guide device using the elongated plates of FIG. 12A. In FIG. 13A, the insertion guide device is illustrated in the collapsed configure. Two of the elongated plates 80 are shown joined by an expandable member 90 which may be any of the embodiments of expandable member disclosed herein. Expandable member 90 is preferably attached to the top surfaces 91 of elongated plates 80 via an adhesive. Expandable member 90 also has a bead 92 to help resist tearing of the expandable member during use. The bead may be a rolled up section of the expandable member to increase thickness and resistance to tearing, or it may be a separate material coupled to the expandable member to provide the reinforcement.

FIG. 13B illustrates the embodiment of FIG. 13A in the expanded configuration.

Figure 14:
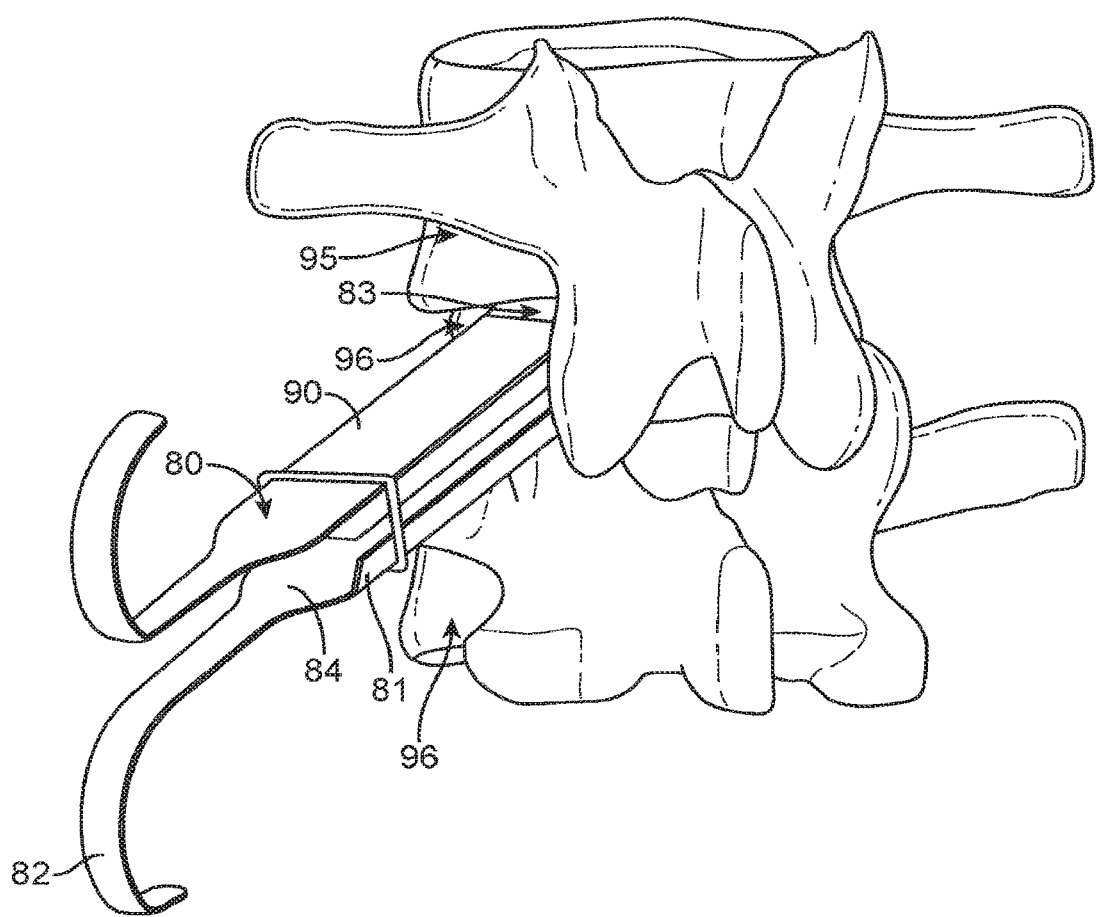
FIG. 14 is a perspective view of the insertion guide device of FIG. 13A inserted into the intervertebral space.

FIG. 14 illustrate the insertion guide device of FIG. 13A inserted into the intervertebral disc space. The insertion guide device is positioned such that the distal portions 83 of the elongated plates 80 engage the endplates of the adjacent vertebral bodies 95 and 96. The expandable member 90 remains outside of the intervertebral space.

Figure 15A:
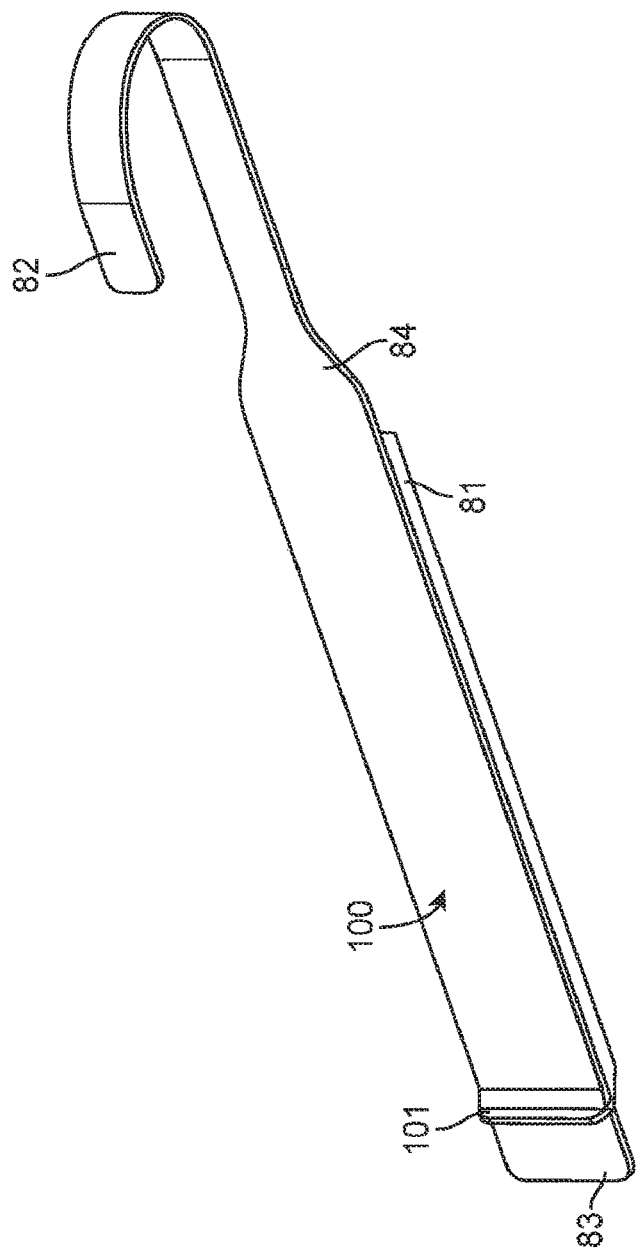
FIG. 15A illustrates a perspective view of another exemplary embodiment of an elongated plate that may be used in an insertion guide device.
Figure 15B:
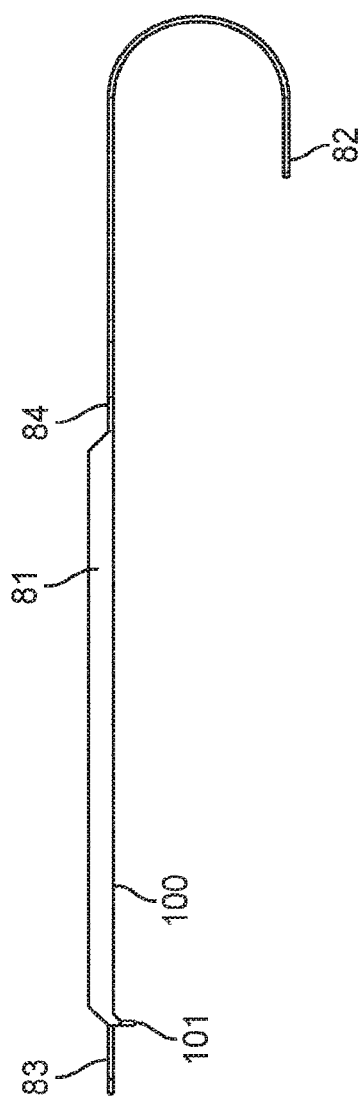
FIG. 15B is a side view of FIG. 15A.

FIGS. 15A-15B illustrate still another exemplary embodiment of elongated plates that may be used in an insertion guide device. FIG. 15A shows an elongated plate 100 with stop feature 101 to prevent the insertion guide device from being inserted too far anteriorly into the disc space. The stop 101 is preferably a protrusion which extends out of the plane of the elongated plate. Other aspects of the elongated plate are generally the same as the embodiment illustrated in FIG. 12A-12B. FIG. 15B is a side view of FIG. 15A.

Figure 16A:
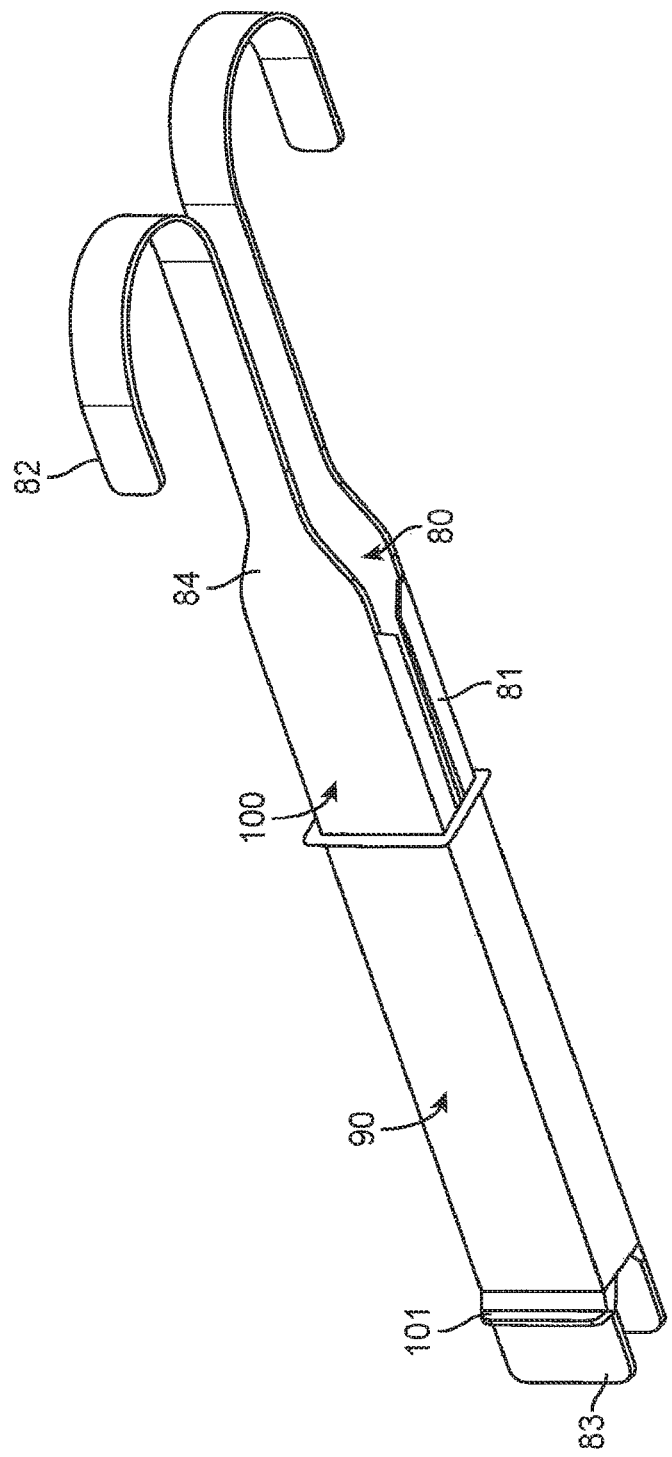
FIG. 16A illustrates a perspective view of an insertion guide device using the elongated plate in FIG. 15A and FIG. 12A, and in the collapsed configuration.
Figure 16B:
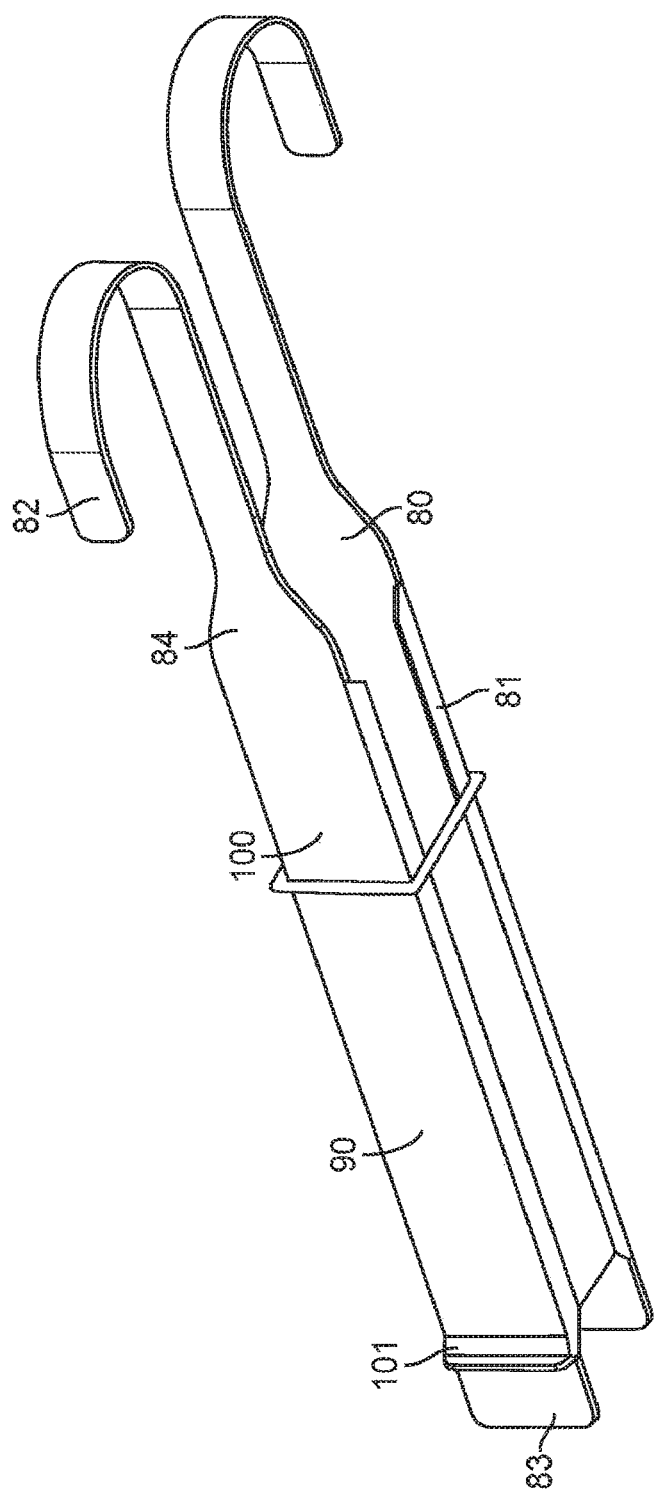
FIG. 16B illustrates the embodiment of FIG. 16A in the expanded configuration.

FIG. 16A illustrates an exemplary embodiment of an insertion guide device using one elongated plate as illustrated in FIG. 15A with a stop, and another elongated plate as illustrated in FIG. 12A without a stop. The embodiment in FIG. 15A is in the collapsed configuration. Expandable member 90 joins elongated plates 80 and 90 together. Other aspects of the insertion guide device are generally the same as previously described above. An alternative embodiment of the insertion guide device may have two elongated plates both having stops. Thus, the insertion guide may have two elongated plates such as those described in FIG. 15A. Other aspects of this alternative embodiment may be the same as those previously described. FIG. 16B illustrates the insertion guide device in FIG. 16A in the expanded (also referred to as distracted) configuration.

Figure 17:
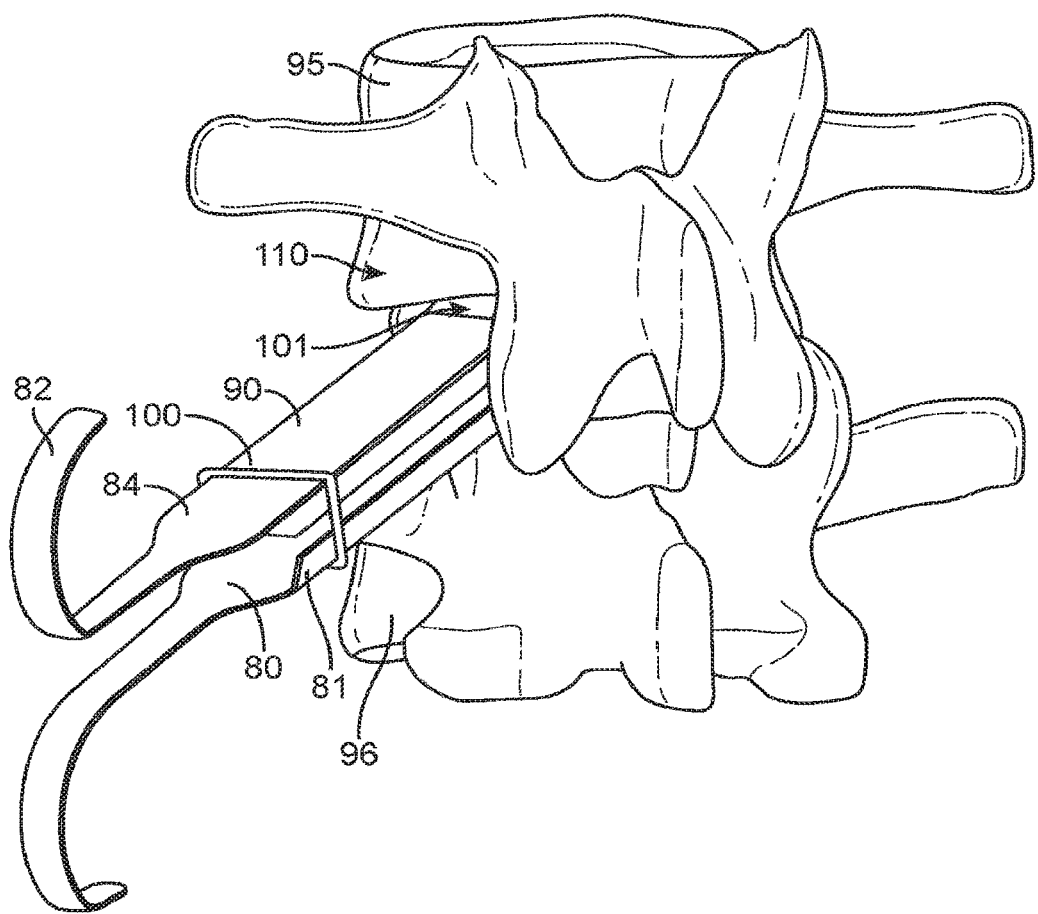
FIG. 17 illustrates the insertion guide device of FIG. 16A inserted into the intervertebral disc space.

FIG. 17 shows the insertion guide device of FIG. 16A inserted into the intervertebral disc space. Stop feature 101 engages the edge of superior vertebral body 110 to prevent the insertion guide device from moving further anterior. In alternative embodiments, the stop feature may engage the edge of the inferior vertebral body 96, or in embodiments with two stops, an edge of the inferior and superior vertebral body may be engaged by a stop feature.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A delivery system for placing an interbody implant into an intervertebral space of a patient, said delivery system comprising:
a first elongated plate having an inner surface, an outer surface, a proximal portion, a distal portion, at least one notch near the distal portion of the first elongated plate, and an external planar surface, wherein the distal portion is sized and shaped to fit into the intervertebral space, and wherein the first elongated plate comprises a first finger loop having an open portion;
a second elongated plate having an inner surface, an outer surface, a proximal portion, a distal portion, and an external planar surface, wherein the distal portion is sized and shaped to fit into the intervertebral space, wherein the first elongated plate is disposed over the second elongated plate, and wherein the second elongated plate comprises a second finger loop having an open portion;
wherein at least one of the first elongated plate and the second elongated plate further comprises one or more rails extending therefrom, wherein the one or more rails are configured to end prior to the distal portion of the respective elongated plate, and wherein the one or more rails are configured to guide the interbody implant; and
an expandable member disposed over and coupled to the outer surfaces of each of the first and second elongated plates, wherein the expandable member is configured to receive the interbody implant, wherein the expandable member is disposed between the proximal and distal portions of the first and second elongated plates such that the expandable member is configured to remain outside of the intervertebral space, wherein the expandable member engages the at least one notch of the first elongated plate to prevent axial migration of the expandable member along a length of the first elongated plate, and wherein the expandable member does not extend past the distal portions of the first and second elongated plates.

2. The delivery system of claim 1, wherein the at least one notch is on a medial edge of the first elongated plate.

3. The delivery system of claim 1, wherein the at least one notch is on a lateral edge of the first elongated plate.

4. The delivery system of claim 1, wherein the at least one notch of the first elongated plate comprises two notches.

5. The delivery system of claim 4, wherein the two notches of the first elongated plate are on opposite sides of the first elongated plate.

6. The delivery system of claim 1, wherein the second elongated plate further comprises at least one notch.

7. The delivery system of claim 6, wherein the at least one notch of the second elongated plate is on a medial edge of the second elongated plate.

8. The delivery system of claim 6, wherein the at least one notch of the second elongated plate is on a lateral edge of the second elongated plate.

9. The delivery system of claim 1, wherein the second elongated plate further comprises two notches.

10. The delivery system of claim 9, wherein the two notches of the second elongated plate are on opposite sides of the second elongated plate.

\* \* \* \* \*